United States Patent [19]
Bormann et al.

[11] 4,112,111
[45] Sep. 5, 1978

[54] INDOLINYLGUANIDINES

[75] Inventors: Gerhard Bormann, Münchenstein; Richard Berthold, Bottmingen, both of Switzerland

[73] Assignee: Sandoz Ltd., Basel, Switzerland

[21] Appl. No.: 819,243

[22] Filed: Jul. 27, 1977

Related U.S. Application Data

[63] Continuation-in-part of Ser. No. 737,443, Nov. 1, 1976, abandoned, which is a continuation-in-part of Ser. No. 659,778, Feb. 20, 1976, abandoned.

[30] Foreign Application Priority Data

Feb. 26, 1975 [CH] Switzerland ............... 2440/75
Aug. 27, 1976 [CH] Switzerland ............... 10883/76

[51] Int. Cl.$^2$ ............... A61K 31/40; C07D 209/08; C07D 209/30; C07D 209/04
[52] U.S. Cl. ............... 424/274; 260/326.11 R
[58] Field of Search ............... 260/326.11 R, 326.15, 260/326.11; 73/744; 424/274; 197/7

[56] References Cited

U.S. PATENT DOCUMENTS

| | | | |
|---|---|---|---|
| 3,478,039 | 11/1969 | Bell | 260/295 |
| 3,565,911 | 2/1971 | Beregi et al. | 260/326.11 R |
| 3,673,188 | 6/1972 | Harsanyi et al. | 260/326.15 |
| 3,823,136 | 7/1974 | Wu et al. | 260/326.11 R |

OTHER PUBLICATIONS

Suvorov et al., Chem. Abstracts, vol. 70, Abstract No. 77701g (1969).

*Primary Examiner*—Alton D. Rollins
*Attorney, Agent, or Firm*—Gerald D. Sharkin; Robert S. Honor; Thomas O. McGovern

[57] ABSTRACT

This invention provides new compounds of formula I,

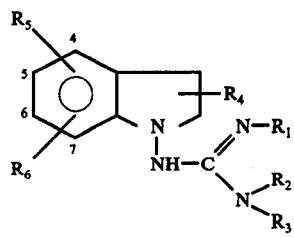

wherein
  $R_1$ to $R_3$ are hydrogen or optionally substituted hydrocarbyl substituents, and
  $R_5$ and $R_6$ are hydrogen, halogen, alkoxy or alkylthio,
useful as anti-hypertensive agents.

29 Claims, No Drawings

INDOLINYLGUANIDINES

This application is a continuation-in-part or our copending application Ser. No. 737,443 filed Nov. 1, 1976, abandoned which is in turn a continuation-in-part of our copending application Ser. No. 659,778 filed Feb. 20, 1976, now abandoned.

The present invention relates to 2-(indolin-1-yl)-guanidine compounds.

The present invention provides compounds of formula I,

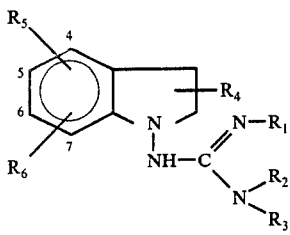

wherein $R_1$ is hydrogen, alkyl of 1 to 4 carbon atoms, phenylalkyl of 7 to 9 carbon atoms, the phenyl ring being unsubstituted or mono- or di-substituted independently by halogen of atomic number of from 9 to 35, or alkyl or alkoxy of 1 to 4 carbon atoms, $R_2$ is (i) hydrogen; (ii) alkyl of 1 to 4 carbon atoms; (iii) phenylalkyl of 7 to 9 carbon atoms, the phenyl ring being unsubstituted or mono- or di-substituted independently by halogen of atomic number of from 9 to 35, or alkyl or alkoxy of 1 to 4 carbon atoms; (iv) alkenyl or alkynyl of 3 to 5 carbon atoms, wherein the multiple bond is other than in the α, β position with respect to the nitrogen to which $R_2$ is attached; (v) hydroxy; (vi) cycloalkyl of 3 to 7 carbon atoms; (vii) alkyl of 1 to 4 carbon atoms monosubstituted by cycloalkyl of 3 to 7 carbon atoms; (viii) phenoxyalkyl of 8 to 11 carbon atoms in the aggregate thereof the oxygen atom thereof being separated by at least two carbon atoms from the nitrogen atom to which $R_2$ is attached, the phenyl ring being unsubstituted or mono- or di-substituted independently by halogen of atomic number of from 9 to 35, or alkyl or alkoxy of 1 to 4 carbon atoms; (ix) aminoalkyl of 2 to 5 carbon atoms, the nitrogen thereof being separated by at least two carbon atoms from the nitrogen atom to which $R_2$ is attached, wherein the amino group is disubstituted by alkyl groups independently of 1 to 4 carbon atoms, or (x) an acetal group

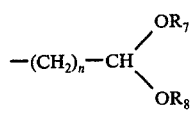

wherein $n$ is a whole number from 1 to 5;

$R_7$ and $R_8$ are independently alkyl of 1 to 4 carbon atoms or together are an alkylene chain of 2 or 3 carbon atoms, $R_3$ and $R_4$ independently are hydrogen, or alkyl of 1 to 4 carbon atoms, and $R_5$ and $R_6$ independently are hydrogen, halogen of atomic number of from 9 to 35 or alkyl, alkoxy or alkylthio of 1 to 4 carbon atoms.

The above-mentioned alkyl, or alkoxy radicals have preferably 2 or especially 1 carbon atom, however, when $R_2$ is alkyl this is preferably a branched alkyl, especially isopropyl.

Halogen substituents are preferably chlorine.

Phenylalkyl radicals are preferably phenethyl or benzyl.

The phenoxyalkyl radical is preferably phenoxyethyl.

Alkenyl or alkynyl is preferably allkyl or 2-propynyl respectively.

Cycloalkyl is preferably cyclopropyl. The alkyl moiety of cycloalkylalkyl has preferably 1 carbon atom, as in cyclopropylmethyl.

Di(alkyl)aminoalkyl is preferably di(alkyl)aminoethyl. Alkylthio is preferably methylthio.

$n$ is preferably 3, especially 1 or 2.

Preferably $R_1$, $R_3$, $R_4$ and $R_6$ are hydrogen, $R_2$ is hydrogen, hydroxy, cycloalkyl, unsubstituted phenylalkyl, or di(alkyl)aminoalkyl, $R_5$ is hydrogen or halogen, preferably chlorine, and $R_7$ and $R_8$ are alkyl.

$R_5$ and/or $R_6$ is preferably in the 6 or 7, especially in the 5 position of the indoline moiety.

The present invention provides a process for the production of a compound of formula I, which comprises reacting a compound of formula II,

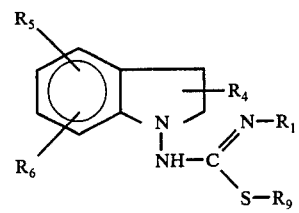

wherein $R_1$, $R_4$, $R_5$ and $R_6$ are as defined above, and $R_9$ is lower alkyl, with a compound of formula III,

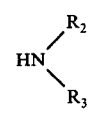

wherein $R_2$ and $R_3$ are as defined above.

$R_9$ has preferably 2 or especially 1 carbon atom.

The process may be effected using known reaction conditions for the production of analogous guanidines.

Conveniently the reaction is affected in the presence of a mineral acid such as hydrochloric, hydrobromic, hydriodic or sulphuric acid.

Preferably at least one equivalent of mineral acid is present calculated on the amount of compound of formula II. Conveniently the compound of formula II or III is used in partly unprotonated form.

The reaction may be conveniently effected in an inert organic solvent or in a fused mixture.

Acid addition salt forms of compounds of formula I may be converted in conventional manner into free base forms and vice versa. Suitable acids include acetic acid, maleic acid, hydrochloric acid, fumaric acid, or naphthalene-1,5-disulphonic acid.

When $R_2$ contains an acetal moiety, then isolation and preparation of acid addition salt forms should be effected under mild conditions due to the acid sensitivity of the acetal moiety.

The compounds of formula II are new and may be obtained analogous to known methods. For example they may be obtained by reacting a compound of formula IV,

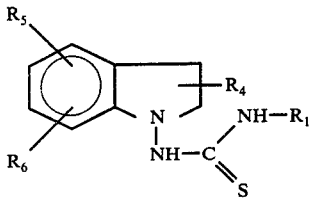

IV wherein $R_1$, $R_4$, $R_5$ and $R_6$ are as defined above, with a compound of formula V, $R_9Hal$  V wherein
  $R_9$ is as defined above, and
  Hal is halogen, preferably iodine.

Compounds of formula IV, wherein $R_1$ is hydrogen may be obtained by reacting in known manner a compound of formula VI,

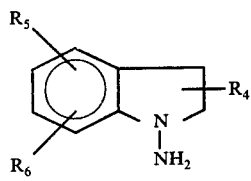

VI wherein $R_4$, $R_5$ and $R_6$ are defined above, with benzoyl isothiocyanate, and splitting off the benzoyl group from the resulting 1-benzoylthiourea.

Compounds of formula IV, wherein $R_1$ is other than hydrogen may be obtained by reacting in known manner a compound of formula VI with a compound of formula VII, $R_1'-N=C=S$  VII wherein
  $R_1'$ is $R_1$ as defined above with the proviso that it is other than hydrogen.

Insofar as the production of any starting material is not particularly described these compounds are known, or may be produced and purified in accordance with known processes, or in a manner analogous to processes described herein, e.g., in the Examples, or to known processes. In the following Examples all temperatures are in degrees centigrade and are uncorrected.

EXAMPLE 1

1-(5-Chloroindolin-1-yl)-3-cyclopropylguanidine 12 g of 1-(5-chloroindolin-1-yl)-2-methylisothiourea hydrochloride in 60 ml of methanol were heated for 5 hours at 100° with 15 ml of cyclopropylamine. The reaction mixture was concentrated to dryness. The residue was partitioned between ethyl acetate and dilute aqueous sodium hydroxide. The ethyl acetate phase was concentrated, and dried over magnesium sulphate to give the title compound. M.Pt. 146° - 149° (on recrystallization from ethyl acetate).

The starting material was obtained as follows:
1-amino-5-chlorindoline was reacted with benzoyl isothiocyanate in boiling tetrahydrofuran. Saponification of the resulting product with dilute aqueous sodium hydroxide under reflux for 15 minutes gave 1-(5-chloroindolin-1-yl)-thiourea (M.Pt. 199° - 200° from ethyl acetate/petroleum ether). This thiourea was heated in boiling methanol in the presence of methyliodide for 1 hour to give 1-(5-chloroindolin-1-yl)-2-methylisothiourea hydroiodide. The base was liberated with aqueous sodium hydroxide. Reaction of the base with 2N ethanolic hydrogen chloride yielded 1-(5-chlorindolin-1-yl)-2-methylisothiourea hydrochloride (M.Pt. 178° - 179° from ethanol/ether).

EXAMPLE 2

1-Hydroxy-3-(indolin-1-yl)guanidine 10 g of 1-(indolin-1-yl)-2-methylisothiourea hydrochloride and 11.4 g of hydroxylamine hydrochloride were suspended in 240 ml of ethanol and were heated to the boil for one hour upon the addition of 6.9 g of potassium ethoxide. Upon cooling, the potassium chloride and the excess hydroxylamine hydrochloride were filtered off with suction and the filtrate was evaporated to dryness. The evaporation residue was partitioned between concentrated aqueous ammonia solution and methylene choride. The methylene chloride solution was dried over magnesium sulphate and evaporated to dryness. 1-hydroxy-3-(indolin-1-yl)guanidine was obtained as an evaporation residue and was crystallized upon the addition of acetic acid, as the acetate from ethanol/ether having a M.Pt. of 155° - 156°.

EXAMPLE 3

1-(5-Chloroindolin-1-yl)-3-(2,2-diethoxyethyl)guanidine 6 g of 1-(5-chlorindolin-1yl)-2-methylisothiourea hydrochloride and 10 ml of aminoacetaldehyde diethyl acetal were heated to a bath temperature of 120° for 1 hour. The excess aminoacetaldehyde diethyl acetal was removed by evaporation in a vacuum and the evaporation residue was partitioned between ethyl acetate and 1N aqueous sodium hydroxide solution. The organic phase was dried over magnesium sulphate and was evaporated to dryness. The 1-(5-chloroindolin-1-yl)-3-(2,2-diethoxyethyl)guanidine obtained as the evaporation residue was crystallized as the naphthalene-1,5-disulphonate having a M.Pt. of 163° -165° (from ethanol/ether).

In analogous manner the following compounds of formula I are obtained from the appropriate compounds of formula II, wherein $R_9$ is methyl and of formula III, wherein $R_1$, $R_3$, $R_4$ and $R_6$ are hydrogen and:

| Ex. No. | $R_2$ | $R_5$ | | M.Pt. |
|---|---|---|---|---|
| 4 | H | H | hnd | 174°-175° |
| 5 | H | 5-Cl | | 153°-155° |
| 6 | H | 6-Cl | | 127°-129° |
| 7 | Cyclopropyl | 6-Cl | hm | 173°-175° |
| 8 | H | 7-Br | hf | 233°-234° |
| 9 | Cyclopropyl | 7-Br | | 153°-156° |
| 10 | Isopropyl | H | hf | 102°-105° |
| 11 | Isopropyl | 5-Cl | hf | 118°-120° |
| 12 | Cyclohexyl | 5-Cl | | 186°-188° |
| 13 | Dimethylaminoethyl | H | bhm | 154°-156° |
| 14 | OH | 5-Cl | hcl | 164°-165° |

-continued

| Ex. No. | R₂ | R₅ | M.Pt. |
|---|---|---|---|
| 15 | Benzyl | 5-Cl | 151°–153° |
| 16 | (2,6-Dichloro-phenoxy)ethyl | H hf | 184°–186° | bhm = Bis[base]hydrogen maleate; hcl = Hydrochloride;
hf = Hydrogen fumarate; hm = Hydrogen maleate; hnd = Hydrogen naphthalene-1,5-disulphonate In the above table Examples 4–13 are effected analogous to Example 1, Example 14 to Example 2 and Examples 15 and 16 to Example 3.

In analogous manner to that described in Example 1 the following compounds of formula I are made, wherein R₃ is methyl and (18d) 6-fluoroindolin-1-ylguanidine. M.Pt. 181° – 183° (hydrochloride)
(18e) 1-(6-fluoroindolin-1-yl)-3-cyclopropylguanidine. M.Pt. 179° – 181° (hydrogen maleate).

The compounds of formula I are useful because they possess pharmacological activity in animals. In particular, the compounds of formula I are useful as salidiuretic agents, e.g., for the treatment of edema and hypertonia as indicated in standard animal tests, for example by an increased secretion of water and sodium chloride from rats on p.o. administration of from about 0.1 to about 100 mg/kg animal body weight of the compounds in accordance with the principles of E. Flückiger et al., Schweiz med. W'schr., 93, 1232–1237 (1963).

Furthermore the compounds lower the blood pressure of experimentally induced hypertonia in Grollman rats on oral and subcutaneous administration at a dose

| R₁ | R₂ | R₄ | R₅ | R₆ |
|---|---|---|---|---|
| 17a) 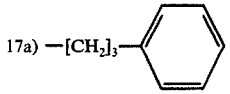 | 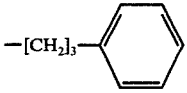 | 3-n-Bu | 4-S-nBu | 6-Br |
| 17b) 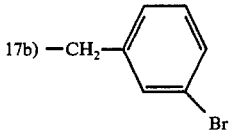 | —CH₂—CH=CH₂ | 2-nBu | 5-nBu | 7-Br |
| 17c) 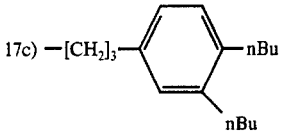 | —CH₂—C≡CH | 2-nBu | 4-nBuO | 6-nBuO |
| 17d) 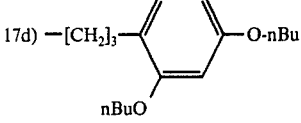 |  | 2-nBu | 4-nBuO | 6-nBuO |
| 17e)  | 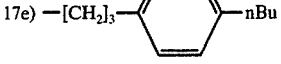 | 2-nBu | 4-nBuO | 6-nBuO |
| 17f) 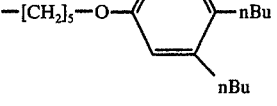 | 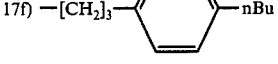 | 2-nBu | 4-nBuO | 6-nBuO |
| 17g) 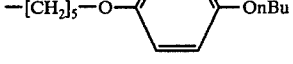 | 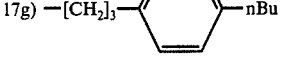 | 2-nBu | 4-nBuO | 6-nBuO |
| 17h) 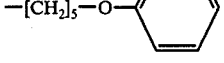 | 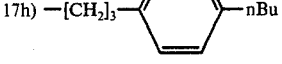 | 2-nBu | 4-nBuO | 6-nBuO |

In analogous manner the following compounds of formula I may be also obtained:
(18a) 4-chloroindolin-1-yl-guanidine. M.Pt. (decomp.) 217° (hydrogen fumarate)
(18b) 1-(4-chloroindolin-1-yl)-3-cyclopropylguanidine. M.Pt. 188° – 190° (hydrochloride)
(18c) 5,7-dichloroindolin-1-ylguanidine. M.Pt. 204° – 205° (hydrogen fumarate)

of 0.3 to 50 mg/kg animal body weight of the compounds according to the principles of A. Grollman [Proc.Soc.Exp.Biol. and Med. 57, 102–104, (1944)].

The anti-hypertensive effect is confirmed in the Goldblatt dog on s.c. administration of from about 1 to about 10 mg/kg animal body weight of the compounds.

For this use the dosage will, of course, vary depending on the compound employed, mode of administration and treatment desired. However, in general, satisfactory results are obtained with a daily dosage of from about 0.01 mg to about 100 mg per kg animal body weight, conveniently given in divided doses 2 to 4 times a day or in sustained release form. For the larger mammal, the total daily dosage is in the range from about 1 to about 50 mg, and dosage forms suitable for oral administration comprise from about 0.25 mg to about 25 mg of the compounds admixed with a solid or liquid pharmaceutical carrier or diluent.

The Example 1 compound is the most interesting compound.

The compounds are also useful for the treatment of venous disorders, such as postural hypotension (e.g., idiopathic and drug induced) and postoperative venous thrombosis, and for the prophylactic treatment of vascular headaches such as migraine. The therapeutic effect is based on the following pharmacological observations:

(a) the direct stimulation of vascular $\alpha$-adrenoceptors, and (b) a selective venotonic action.

$\alpha$-Adrenoceptor stimulation was demonstrated by a pressor effect in the pithed rat experiment following i.v. administration of from 1 to 200 $\mu$g/kg of the compounds, elicited a 30 to 170% increase in blood pressure.

This pressor effect is antagonised by phentolamine, but is not significantly influenced by reserpine. A similar action of phentolamine and reserpine is observed on the contractions of the nictitating membrane in the spinal cat.

The selective venotonic effect was shown in the acutely denervated cat calf muscle vasculature. On i.a. administration the compounds (5 to 45 $\mu$g/kg) did not significantly change the resistance values but there was a decrease in venous capacitance of between 0.24 and 0.6 ml/100 g tissues.

The compound of Example 18a) exhibits particularly interesting properties.

For the above-mentioned uses the dosage will, of course, vary depending on the compound employed, mode of administration and therapy desired. However, in general, satisfactory results are obtained when administered at a daily dosage of from 1 $\mu$g to about 200 $\mu$g per kg animal body weight, conveniently given in divided doses 2 to 4 times a day or in sustained release form. For the larger mammal, the total daily dosage is in the range from about 1 to about 20 mg, and dosage form suitable for oral administration comprise from about 0.2 mg to about 10 mg of the compounds admixed with a solid or liquid pharmaceutical carrier or diluent.

The compounds of formula I may be administered in pharmaceutically acceptable acid addition salt forms. These have the same order of activity as the free base forms. Suitable salt forms include the naphthalene-1,5-disulphonate and acetate.

The compounds of formula I may be administered in pharmaceutically acceptable acid addition salt form. Such acid addition salt forms exhibit the same order of activity as the free base forms, and are readily prepared in conventional manner. The present invention also provides a pharmaceutical composition comprising a compound of formula I, in free base form or in pharmaceutically acceptable acid addition salt form, in association with a pharmaceutical carrier or diluent. Such compositions may be in the form of, for example, a solution or a tablet.

In one group of compounds $R_2$ is hydrogen, alkyl, phenylalkyl, alkenyl, alkynyl, hydroxy, cycloalkyl, cycloalkylmethyl or the acetal group defined above.

Preferred compounds of formula I are compounds of formula Iw,

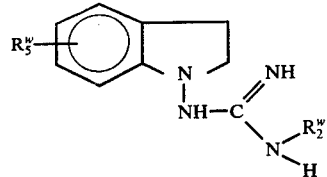

wherein
$R_2^w$ is hydrogen, hydroxy, cycloalkyl of 3 to 6 carbon atoms, phenylalkyl, or aminoalkyl of 2 to 3 carbon atoms, wherein the amino group is disubstituted by alkyl groups independently of 1 or 2 carbon atoms, and $R_5^w$ is hydrogen or halogen of atomic number of from 9 to 35.

In one group of compounds $R_1$, $R_3$, $R_4$ and $R_6$ are all hydrogen.

In another group of compounds $R_2$ is significance (i).
In a further group of compounds $R_2$ is significance (ii).
In a further group of compounds $R_2$ is significance (iii).
In a further group of compounds $R_2$ is significance (iv).
In a further group of compounds $R_2$ is significance (v).
In a further group of compounds $R_2$ is significance (vi).
In a further group of compounds $R_2$ is significance (vii).
In a further group of compounds $R_2$ is significance (viii).
In a further group of compounds $R_2$ is significance (ix).
In a further group of compounds $R_2$ is significance (x).

$R_5$ in each of the above groups may be conveniently hydrogen or alkyl.

In a group of compounds $R_2$ is phenoxyalkyl unsubstituted, mono-substituted by alkoxy, preferably in the para position, or mono- or di-substituted by halogen or alkyl.

In a group of compounds $R_2$ is other than hydrogen and $R_3$ is hydrogen or methyl.

We claim:
1. A compound of formula I,

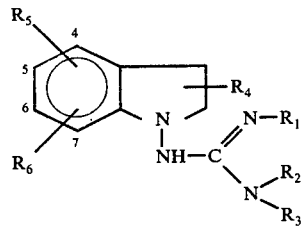

wherein
$R_1$ is hydrogen, alkyl of 1 to 4 carbon atoms, phenylalkyl of 7 to 9 carbon atoms, the phenyl ring being unsubstituted or mono- or di-substituted independently by halogen of atomic number of from 9 to 35, or alkyl or alkoxy of 1 to 4 carbon atoms, $R_2$ is (i) hydrogen; (ii) alkyl of 1 to 4 carbon atoms; (iii) phenylalkyl of 7 to 9 carbon atoms, the phenyl ring being unsubstituted or mono- or di-substituted independently by halogen of atomic number of from 9 to 35, or alkyl or alkoxy of 1 to 4 carbon atoms; (iv) alkenyl or alkynyl of 3 to 5 carbon atoms, wherein the multiple bond is other than in the α,β position with respect to the nitrogen to which $R_2$ is attached; (v) hydroxy; (vi) cycloalkyl of 3 to 7 carbon atoms; (vii) alkyl of 1 to 4 carbon atoms monosubstituted by cycloalkyl of 3 to 7 carbon atoms; (viii) phenoxyalkyl of 8 to 11 carbon atoms in the aggregate thereof, the oxygen atom thereof being separated by at least two carbon atoms from the nitrogen atom to which $R_2$ is attached, the phenyl ring being unsubstituted or mono- or di-substituted independently by halogen of atomic number of from 9 to 35, or alkyl or alkoxy of 1 to 4 carbon atoms; (ix) aminoalkyl of 2 to 5 carbon atoms, the nitrogen thereof being separated by at least two carbon atoms from the nitrogen atom to which $R_2$ is attached, wherein the amino group is disubstituted by alkyl groups independently of 1 to 4 carbon atoms, or (x) an acetal group

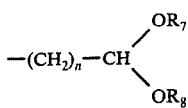

wherein n is a whole number from 1 to 5;

$R_7$ and $R_8$ are independently alkyl of 1 to 4 carbon atoms or together are an alkylene chain of 2 or 3 carbon atoms, $R_3$ and $R_4$ independently are hydrogen, or alkyl of 1 to 4 carbon atoms, and $R_5$ and $R_6$ independently are hydrogen, halogen of atomic number of from 9 to 35 or alkyl, alkoxy or alkylthio of 1 to 4 carbon atoms, in free base form or in pharmaceutically acceptable acid addition salt form.

2. A method of treating oedema or hypertension in animals which comprises administering a therapeutically effective amount of a compound of claim 1 to an animal in need of such treatment.

3. A compound of claim 1, wherein $R_1$ is hydrogen, $R_2$ is hydrogen or cyclopropyl, $R_3$ is hydrogen and $R_4$ is hydrogen.

4. A compound of claim 1, wherein $R_2$ is hydrogen, alkyl, phenylalkyl, alkenyl, alkynyl, hydrodxy, cycloalkyl, cycloalkylmethyl, or the acetal group as defined in claim 1.

5. A compound of claim 1 having the formula Iw,

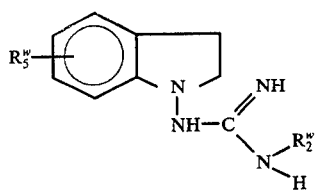

wherein $R_2^w$ is hydrogen, hydroxy, cycloalkyl of 3 to 6 carbon atoms, phenylalkyl, or aminoalkyl of 2 to 3 carbon atoms, wherein the amino group is disubstituted by alkyl groups independently of 1 or 2 carbon atoms, and $R_5^w$ is hydrogen or halogen of atomic number of from 9 to 35.

6. A compound of claim 1, wherein $R_1$, $R_3$, $R_4$ and $R_6$ are all hydrogen.

7. A method of treating orthostatic disorders or treating or preventing vascular headaches in animals comprising administering to an animal in need of such treatment a therapeutically effective amount of a compound of formula I.

8. A composition for treating edema, hypertension, orthostatic disorders, or vascular headaches in animals comprising a compound of claim 1 in an amount effective for treatment of the above named conditions in association with a pharmaceutical carrier or diluent.

9. The compound of claim 6, wherein $R_2$ and $R_5$ are respectively H and H.

10. The compound of claim 6, wherein $R_2$ and $R_5$ are respectively H and 5-Cl.

11. The compound of claim 6, wherein $R_2$ and $R_2$ are respectively H and 6-Cl.

12. The compound of claim 6, wherein $R_2$ and $R_5$ are respectively cyclopropyl and 6-Cl.

13. The compound of claim 6, wherein $R_2$ and $R_5$ are respectively H and 7-Br.

14. The compound of claim 6, wherein $R_2$ and $R_5$ are respectively cyclopropyl and 7-Br.

15. The compound of claim 6, wherein $R_2$ and $R_5$ are respectively isopropyl and H.

16. The compound of claim 6, wherein $R_2$ and $R_5$ are respectively isopropyl and 5-Cl.

17. The compound of claim 6, wherein $R_2$ and $R_5$ are respectively cyclohexyl and 5-Cl.

18. The compound of claim 6, wherein $R_2$ and $R_5$ are respectively dimethylaminoethyl and H.

19. The compound of claim 6, wherein $R_2$ and $R_3$ are respectively OH and 5-Cl.

20. The compound of claim 6, wherein $R_2$ and $R_5$ are respectively benzyl and 5-Cl.

21. The compound of claim 6, wherein $R_2$ and $R_5$ are respectively (2,6-dichlorophenoxy) ethyl and H.

22. The compound of claim 6, which is 4-chloroindolin-1-yl-guanidine.

23. The compound of claim 6, which is 6-fluoroindolin-1-ylguanidine.

24. The compound of claim 6, which is 1-(5-chloroindolin-1-yl)-3-cyclopropylguanidine.

25. The compound of claim 6, which is 1-hydroxy-3-(indolin-1-yl) guanidine.

26. The compound of claim 6, which is 1-(5-chloroindolin-1-yl)-3-(2,2-diethoxyethyl) guanidine.

27. The compound of claim 6, which is 1-(4-chloroindolin-1-yl)-3-cyclopropylguanidine.

28. The compound of claim 1, which is 5,7-dichloroindolin-1-ylguanidine.

29. The compound of claim 6, which is 1-(6-fluoroindolin-1-yl)-3-cyclopropylguanidine.

* * * * *